United States Patent [19]

Howe et al.

[11] 4,398,941

[45] Aug. 16, 1983

[54] HERBICIDAL COMPOSITION AND METHOD

[75] Inventors: Robert K. Howe, Bridgeton; Len F. Lee, St. Charles, both of Mo.

[73] Assignee: Monsanto Company, St. Louis, Mo.

[21] Appl. No.: 356,010

[22] Filed: Mar. 8, 1982

[51] Int. Cl.³ .................. C07D 279/12; C07D 295/08; C07D 295/10; A01N 43/84
[52] U.S. Cl. ........................................ 71/90; 544/58.4
[58] Field of Search ........................... 544/58.4; 71/90

[56] References Cited

U.S. PATENT DOCUMENTS 2,191,452  2/1940  Coghill .............................. 544/58.4

Primary Examiner—John M. Ford
Attorney, Agent, or Firm—Arnold H. Cole; Howard C. Stanley; Raymond C. Loyer

[57] ABSTRACT

The invention herein pertains to dialkyl 3,5-bis(perfluoroalkyl)-2H-1,4-thiazine-2,6-dicarboxylates, a method for preparing the compounds and to herbicidal compositions and methods utilizing said compounds.

49 Claims, No Drawings

HERBICIDAL COMPOSITION AND METHOD

This invention relates to novel compounds useful as herbicides. The compounds may be represented by the formula

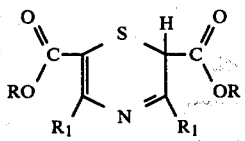

wherein R is selected from the group consisting of H and lower alkyl radicals and $R_1$ represents a perfluoroalkyl radical.

The term "lower alkyl" is intended to mean alkyl radicals having up to and including 4 carbon atoms.

The term "perfluoroalkyl radicals" is intended to mean alkyl radicals having up to and including 3 carbon atoms wherein all of the hydrogen atoms have been replaced with fluorine atoms.

In accordance with one of the novel aspects of this invention, the compounds can be prepared by the reaction of the appropriate 3-perfluoroalkyl-3-aminoacrylate with either sulfur monochloride or sulfur dichloride. In one embodiment, the reaction provides a mixture containing a major amount of the thiazine compound of this invention and a minor but significant amount of corresponding pyrroledicarboxylates. However, the order of addition of the reactant has been discovered to be influential in controlling the ratio of reaction products. Thus, by adding the 3-perfluoroalkyl-3-amino acrylate to the sulfur mono- or dichloride, there is provided a greatly increased amount of the thiazine dicarboxylate of this invention with a corresponding decrease in the production of pyrroledicarboxylate. Regardless of the order of addition of the reactants to the reaction vessel, the reaction proceeds as follows:

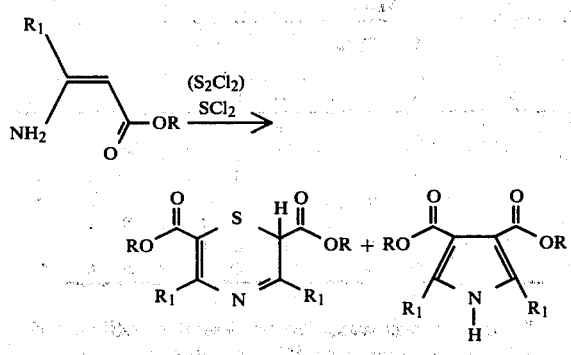

The product can be readily separated by HPLC on silica gel using ethyl acetate-petroleum ether as eluant. The above reaction is typically initiated at relatively low temperatures such as −5° C. to +5° C. The reaction mixture is allowed to warm as the reaction proceeds and addition of heat is applied as the temperature reaches ambient condition. Generally, the reaction is completed at a temperature in the range of from 40° C. to 60° C. Although not critical, the reaction time extends for a period of about 3 hours at the elevated temperature. However, individual reactants have varying reaction rates and, of course, temperature level also affects the reaction rate.

As mentioned above, either sulfur monochloride or sulfur dichloride may be employed. However, experience indicates that higher yields of the desired thiazine is obtained utilizing sulfur dichloride.

Any suitable reaction medium may be employed and typically it is selected from the common organic hydrocarbons and halogenated hydrocarbons. Typical media are chlorobenzene, $C_{6-10}$ hydrocarbons such as hexane and commercially available mixed hydrocarbons.

The above-described thiazines are useful as pre- and post-emergent selective herbicides. Since they are provided in admixture with the pyrroledicarboxylates, the herbicidal compositions described and claimed herein may contain a minor amount, for example, under 5% by weight of the pyrroledicarboxylate but will be referred to herein as simply thiazine compositions. The presence of the pyrroledicarboxylate does not inhibit the herbicidal activity of the thiazine compounds of this invention.

The β-aminoarylates utilized in the above-described reaction may be prepared according to known procedures such as that specified in Lutz et al, Journal of Heterocyclic Chemistry, Volume 9, Page 513 (1972) or they may be prepared by mixing 0.5 moles of ethyl acetoacetate or methyl acetoacetate in 200 ml. of methanol and 100 ml. of saturated sodium acetate and passing through the appropriate nitrile (perfluorinated for this purpose) for several hours. The reaction mixture is poured into ice water and the organic layer extracted with ether. The ether solution is dried and concentrated and the residue is distilled. A mixture of about 0.1 mole of said distillate and 50 ml. of 30% ammonium hydroxide or sodium hydroxide is stirred from 1 to 4 hours. The reaction mixture is extracted with methylene chloride and the methylene chloride extracts dried and concentrated. Fractional distillation of the residue results in the 3-perfluoroalkyl-3-aminoacrylate.

In order to more fully describe the manner in which the thiazole herbicides of this invention are prepared, the following non-limiting examples are presented.

EXAMPLE 1

Preparation of Diethyl 2H-1,4-Thiazine-3,5-bis(Pentafluoroethyl)-2,6-Ethyldicarboxylate To a well stirred cold (−3° C.) solution of 2.1 g (0.02 mol) of $SCl_2$ in 100 ml. of chlorobenzene is added dropwise a solution of 9.32 g (0.04 mol) of ethyl 3-amino-4,4,5,5,5-pentafluoro-2-pentenoate in 10 ml. of chlorobenzene in 10 minutes. The reaction mixture is heated to 50° C. in 55 minutes and maintained at 50° C. for 3 hours. The reaction mixture is filtered and washed with hexane. The combined filtrate is concentrated under reduced pressure and the residual oil (10.4 g) is kugelrohr distilled at 1 mm (pot temperature 110° C.) to give 7.96 g (83%) of the desired product $n_D^{25}$ 1.4140.

Anal. Calc'd for $C_{14}H_{11}F_{10}NO_4S$: C, 35.08; H, 2.31; N, 2.92. Found: C, 35.39; H, 2.15; N, 2.96.

In a manner similar to Example 1, other thiazines of this invention are prepared by the reaction of the appropriate β-aminoacrylate and sulfur chloride as indicated below in Table I.

TABLE I

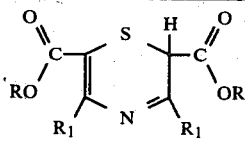

| Ex. No. | R | $R_1$ | Chloride | M.P. °C. | $N_D^{25}$ | Empirical Formula | Calc'd C | H | N | Found C | H | N |
|---|---|---|---|---|---|---|---|---|---|---|---|---|
| 2 | $C_2H_5$ | $CF_3$ | $S_2Cl_2$ | | 1.4395 | $C_{12}H_{11}F_6NO_4S$ | 38.00 | 2.92 | 3.69 | 38.15 | 2.98 | 3.69 |
| 3 | $C_2H_5$ | $C_3F_7$ | $SCl_2$ | | 1.4011 | $C_{16}H_{11}F_{14}NO_4S$ | 33.17 | 1.91 | 2.42 | 33.32 | 1.81 | 2.36 |
| 4 | $CH_3$ | $C_2F_5$ | $SCl_2$ | 33.5–36 | | $C_{12}H_7F_{10}NO_4S$ | 31.94 | 1.56 | 3.10 | 31.91 | 1.58 | 3.10 |
| 5 | $C_4H_9$ | $C_2F_5$ | $SCl_2$ | | 1.4270 | $C_{18}H_{18}F_{10}NO_4S$ | 40.44 | 3.37 | 2.62 | 40.58 | 3.43 | 2.68 |

EXAMPLE 6

Preparation of 3,5-bis(Pentafluoroethyl)-2H-1,4-Thiazine-2,6-Dicarboxylic Acid

A mixture of 5.0 g (0.0111 mole) of the compound of Example 4, and 8.88 g (0.0444 mole) of trimethylsilyl iodide is held at 105° C. for 22 hours. The reaction mixture is then stirred with petroleum ether and filtered. The petroleum ether filtrate is washed with water, dried ($MgSO_4$) and concentrated to give 3.55 g of an oil which is crystallized from chloroform-petroleum ether to give 1.78 g (37.9%) of the desired product as a solid. M.P. 108°–112° C.

Anal. Calc'd for $C_{10}H_3F_{10}NO_4S$: C, 28.38; H, 0.71; N, 3.31; S, 7.58. Found: C, 28.48, H, 0.99; N, 3.34; S, 7.57.

As noted above, the compounds of this invention have been found to be effective as herbicides, in some instances both pre-emergent as well as post-emergent. Tables II and III summarize results of tests conducted to determine the pre-emergent herbicidal activity of the compounds of this invention. Table IV and V summarize results of tests conducted to determine the post-emergent herbicidal activity of the compounds of this invention.

The pre-emergent tests are conducted as follows:

A good grade of top soil is placed in aluminum pans and compacted to a depth of three-eighths to one-half inch from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable power suspension and the soil are thoroughly mixed, and used as a cover layer for prepared pans. After treatment, the pans are moved into a greenhouse bench where they are watered from below as needed to give adequate moisture for germination and growth.

Approximately 2–3 weeks after seeding and treating, the plants are observed and the results recorded. Table II below summarizes such results. The herbicidal rating is obtained by means of a fixed scale based on the percent injury of each plant species. The ratings are defined as follows:

| % Control | Rating |
|---|---|
| 0–24 | 0 |
| 25–49 | 1 |
| 50–74 | 2 |
| 75–100 | 3 |

The plant species utilized in one set of tests, the data for which are shown in Table II, are identified by letter in accordance with the following legend:

| A | Canada Thistle* | E | Lambsquarters | I | Johnsongrass* |
| B | Cocklebur | F | Smartweed | J | Downy Brome |
| C | Velvetleaf | G | Yellow Nutsedge* | K | Barnyardgrass |
| D | Morningglory | H | Quackgrass* | | |

*Grown from vegetative propagules.

TABLE II

| Compound of Example No. | WAT | kg/h | Pre-Emergent Plant Species | | | | | | | | | | |
|---|---|---|---|---|---|---|---|---|---|---|---|---|---|
| | | | A | B | C | D | E | F | G | H | I | J | K |
| 2 | 2 | 11.2 | 1 | 0 | 3 | — | 3 | 1 | 0 | 0 | 0 | 0 | 1 |
| 3 | 2 | 11.2 | 0 | 0 | 1 | 1 | 3 | 2 | 0 | 0 | 0 | 1 | 0 |
| 1 | 2 | 11.2 | 2 | 3 | 3 | 3 | 3 | 3 | 0 | 0 | 0 | 1 | 0 |
| 4 | 2 | 11.2 | 3 | 0 | 0 | 3 | 2 | 1 | 0 | 0 | 0 | 2 | 3 |
| | 4 | 11.2 | 3 | 0 | 0 | 2 | 3 | 0 | 0 | 0 | 0 | 2 | 3 |
| 6 | 2 | 11.2 | 1 | 0 | 0 | 0 | 0 | 0 | 0 | 0 | 0 | 0 | 0 |
| 7 | 2 | 11.2 | 0 | 0 | 0 | 0 | 2 | 0 | 0 | 0 | 0 | 0 | 0 |

The compounds were further tested by utilizing the above procedure on the following plant species:

| L | Soybean | R | Hemp Sesbania |
| M | Sugarbeet | E | Lambsquarters |
| N | Wheat | F | Smartweed |
| O | Rice | C | Velvetleaf |
| P | Sorghum | J | Downy Brome |
| B | Cocklebur | S | Panicum |
| Q | Wild Buckwheat | K | Barnyardgrass |
| D | Morningglory | T | Crabgrass |

The results are summarized in Table III.

4,398,941

TABLE III

| Compound of Example No. | kg/ha | L | M | N | O | P | B | Q | D | R | E | F | C | J | S | K | T |
|---|---|---|---|---|---|---|---|---|---|---|---|---|---|---|---|---|---|
| 2 | 5.6 | 0 | 3 | 0 | 0 | 0 | 0 | 0 | 2 | 3 | 3 | 1 | 3 | 0 | 0 | 0 | 0 |
|   | 1.12 | 0 | 2 | 0 | 1 | 0 | 0 | 0 | 0 | 3 | 3 | 0 | 0 | 0 | 0 | 0 | 0 |
| 1 | 11.2 | 0 | 3 | 0 | 0 | 0 | 0 | 2 | 3 | 3 | 3 | 3 | 1 | 1 | 0 | 1 | 1 |
|   | 5.6 | 0 | 3 | 0 | 0 | 0 | 0 | 0 | 3 | 1 | 3 | 3 | 3 | 0 | 0 | 0 | 1 |
|   | 1.12 | 0 | 3 | 0 | 0 | 0 | 0 | 0 | 1 | 0 | 3 | 0 | 0 | 0 | 0 | 0 | 1 |
|   | .28 | 0 | 3 | 0 | 0 | 0 | 0 | 3 | 0 | 1 | 3 | 0 | 0 | 0 | 0 | 0 | 1 |
| 4 | 5.6 | 2 | 3 | 0 | 0 | 0 | 0 | 1 | 2 | 2 | 3 | 1 | 0 | 2 | 0 | 1 | — |
|   | 1.12 | 0 | 2 | 0 | 0 | 0 | 0 | 0 | 0 | 0 | 0 | 0 | 0 | 0 | 0 | 1 | — |
|   | .28 | 0 | 1 | 0 | 0 | 0 | 0 | 0 | 0 | 0 | 0 | 0 | 0 | 0 | 0 | 1 | — |

The post emergent tests were conducted as follows. The herbicidal active ingredients were applied in spray form to two or three-week old specimens of various plant species. The spray, a solution or wettable powder suspension containing the appropriate rate of herbicidal active ingredient to give the desired test rate and a surfactant, was applied to the plants at a pressure of 3.62 g/mm.$^2$. The surfactant is an amine salt of an alkylbenzene sulfonic acid blended with an ethoxylated tall oil. The spray volume is regulated to apply at the rate of about 850 L/ha. The treated plants were placed in a greenhouse and approximately two or four weeks later the effects were observed and recorded. The results are shown in Tables IV and V in which the post-emergent herbicidal rating code is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the previous legend.

TABLE IV

| Compound of Example No. | WAT | kg/h | A | B | C | D | E | F | G | H | I | J | K |
|---|---|---|---|---|---|---|---|---|---|---|---|---|---|
| 2 | 2 | 11.2 | 2 | 2 | 1 | 3 | 3 | 3 | 0 | 0 | 2 | 0 | 3 |
| 3 | 2 | 11.2 | 0 | 1 | 1 | 1 | 1 | 0 | 0 | 0 | 1 | 0 | 2 |
| 1 | 2 | 11.2 | 3 | 3 | 3 | — | 3 | 4 | 1 | 0 | 1 | 2 | 3 |
| 4 | 2 | 11.2 | 1 | 1 | 1 | 1 | 1 | 0 | — | 1 | 0 | 0 | 1 |
| 6 | 2 | 11.2 | — | 3 | 1 | 3 | 2 | 2 | — | 0 | 0 | 0 | 1 |
| 5 | 2 | 11.2 | 1 | 1 | 1 | 0 | 1 | — | 0 | 0 | 0 | 0 | 1 |
| 7 | 2 | 11.2 | 4 | 1 | 0 | 2 | 0 | 2 | 0 | 0 | 0 | 0 | 0 |

TABLE V

| Compound of Example No. | kg/ha | L | M | N | O | P | B | Q | D | R | E | F | C | J | S | K | T |
|---|---|---|---|---|---|---|---|---|---|---|---|---|---|---|---|---|---|
| 2 | 5.6 | 1 | 4 | 1 | 1 | 2 | 2 | 3 | 3 | 4 | 3 | 4 | 1 | 0 | 1 | 1 | 2 |
|   | 1.12 | 1 | 0 | 1 | 0 | 1 | 0 | 0 | 1 | 1 | 3 | 1 | 0 | 0 | 0 | 0 | 1 |
| 1 | 5.6 | 2 | 4 | 1 | 1 | 1 | 4 | 4 | 4 | 2 | — | 4 | 4 | 1 | 1 | 2 | 1 |
|   | 1.12 | 1 | 4 | 0 | 0 | 0 | 1 | 0 | 0 | 0 | 2 | 2 | 0 | 0 | 0 | 0 | 0 |

The above tables illustrate one aspect of the present invention, that is, the use of the compounds of the invention to kill or injure undesirable plants, e.g., weeds.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containining a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total suspension, preferably 480 to 600 g/l.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihyrodipyrido(1,2-a:2',1'-c)-pyrazidiinium salt
5-Bromo-3-isopropyl-6-methyluracil
1,1'-Dimethyl-4,4'-bipyridinium.

Ureas

N'-(4-chlorophenoxy) phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea.

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate.

Acetamides/Acetanilides/Anilines/Amides

2-Chloro-N,N-diallylacetamide
N,N-dimethyl-2,2-diphenylacetamide
N-(2,4-dimethyl-5-[(trifluoromethyl)sulfonyl amino]-phenylacetamide
N-Isopropyl-2-chloroacetanilide
2',6'-Diethyl-N-methoxymethyl-2-chloroacetanilide 2'-Methyl-6'-ethyl-N-(2-methoxyprop-2-yl)-2-chloroacetanilide $\alpha,\alpha,\alpha$-Trifluoro-2,6-dinitro-N,N-dipropyl-p-toluidine N-(1,1-dimethylpropynyl)-3,5-dichlorobenzamide.

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
3-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof.

Ethers 2,4-Dichlorophenyl-4-nitrophenyl ether
2-Chloro-$\alpha,\alpha,\alpha$-trifluoro-p-tolyl-3-ethoxy-4-nitrodiphenyl ether.

Miscellaneous 2,6-Dichlorobenzonitrile
Monosodium acid methanearsonate Disodium methanearsonate.

Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| I. Emulsifiable Concentrates | | Weight Percent |
|---|---|---|
| A. | Compound of Example No. 1 | 1.0 |
| | Free acid of complex organic phosphate of aromatic or aliphatic hydrophobe base (e.g., GAFAC RE-610, registered trademark of GAF Corp) | 5.59 |
| | Polyoxyethylene/polyoxypropylene block copolymer with butanol (e.g., Tergitol XH, registered trademark of Union Corp.) | 1.11 |
| | Phenol | 5.34 |
| | Monochlorobenzene | 77.16 |
| | | 100.00 |
| B. | Compound of Example No. 3 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |

| II. Flowables | | Weight Percent |
|---|---|---|
| A. | Compound of Example No. 2 | 25.00 |
| | Methyl cellulose | 0.3 |
| | Silica aerogel | 1.5 |
| | Sodium lignosulfonate | 3.5 |
| | Sodium N—methyl-N—oleyl taurate | 2.0 |
| | Water | 66.7 |
| | | 100.00 |
| B. | Compound of Example No. 4 | 45.0 |
| | Methyl cellulose | .3 |
| | Silica aerogel | 1.5 |
| | Sodium lignosulfonate | 3.5 |
| | Sodium N—methyl-N—oleyl taurate | 2.0 |
| | Water | 47.3 |
| | | 100.00 |

| III Wettable Powders | | Weight Percent |
|---|---|---|
| A. | Compound of Example No. 5 | 25.0 |
| | Sodium lignosulfonate | 3.0 |
| | Sodium N—methyl-N—oleyl-taurate | 1.0 |
| | Amorphous silica (synthetic) | 71.0 |
| | | 100.00 |
| B. | Compound of Example No. 6 | 80.0 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 2 | 10.0 |
| | Sodium lignosulfonate | 3.0 |
| | Sodium N—methyl-N—oleyl-taurate | 1.0 |
| | Kaolinite clay | 86.0 |
| | | 100.00 |

| IV. Water-Soluble Powders | | Weight Percent |
|---|---|---|
| A. | Compound of Example 4 | 10.0 |
| | Sodium dioctyl sulfosuccinate | 2.0 |
| | Silica aerogel | 5.0 |
| | Methyl violet | 0.1 |
| | Sodium bicarbonate | 82.9 |
| | | 100.00 |
| B. | Compound of Example No. 1 | 90.0 |
| | Ammonium phosphate | 10.0 |
| | | 100.00 |

| V. Dusts | | Weight Percent |
|---|---|---|
| A. | Compound of Example No. 3 | 2.0 |
| | Attapulgite | 98.0 |
| | | 100.00 |
| B. | Compound of Example No. 1 | 60.0 |
| | Montmorillonite | 40.0 |
| | | 100.00 |
| C. | Compound of Example No. 6 (cis) | 30.0 |
| | Ethylene glycol | 1.0 |
| | Bentonite | 69.0 |
| | | 100.00 |
| D. | Compound of Example No. 3 | 1.0 |
| | Diatomaceous earth | 99.0 |
| | | 100.00 |

| VI. Granules | | Weight Percent |
|---|---|---|
| A. | Compound of Example No. 2 | 15.0 |
| | Granular attapulgite (20/40 mesh) | 85.0 |
| | | 100.00 |
| B. | Compound of Example No. 4 | 30.0 |
| | Diatomaceous earth (20/40) | 70.0 |
| | | 100.00 |
| C. | Compound of Example No. 7 | 1.0 |
| | Ethylene glycol | 5.0 |
| | Methylene blue | 0.1 |
| | Pyrophyllite | 93.9 |
| | | 100.00 |
| D. | Compound of Example No. 5 | 5.0 |
| | Pyrophyllite (20/40) | 95.0 |
| | | 100.00 |

When operating in accordance with the present invention, effective amounts of the herbicide of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific compounds employed. In selective preemergence application to the plants or to the soil a dosage of from 0.02 to about 11.2 kg/ha, preferably from about 0.04 to about 5.60 kg/ha, or suitably from 1.12 to 5.6 kg/ha of herbicide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

There has also been discovered novel compounds which are intermediates for the novel thiazine compounds of this invention. The intermediates can be utilized to make the thiazine compounds of this invention by crystallization from solution.

The intermediate compounds are represented by the formula

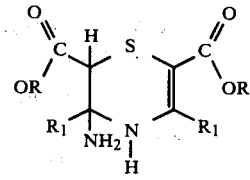

wherein R and $R_1$ have the meaning given above.

A typical example for the production of the novel intermediates is as follows:

EXAMPLE 7

Preparation of Diethyl 3-Amino-3,5-bis(Trifluoromethyl)-3,4-Dihydro-2H-1,4-Thiazine-2,6-Dicarboxylate To a cold (10° C.) solution of 10.3 g (0.10 mole) of sulfur dichloride in 50 ml. of ether is added a solution of 36.8 g (0.20 mole) of ethyl 3-amino-4,4,4-trifluorocrotonate in 20 ml. of ether over a period of 50 minutes. The reaction mixture is maintained below 25° C. by an ice water bath. After 1 hour of stirring, the reaction mixture is poured into 200 ml. of saturated sodium bicarbonate slowly with vigorous stirring. The ether layer is separated, dried ($MgSO_4$) and concentrated. The residue is triturated with petroleum ether to give 19 g (48%) of the desired product. M.P. 87.5°-9° C.

Anal. Calc'd for $C_{12}H_{14}F_6N_2O_4S$: C, 36.36; H, 3.56; N, 7.07; S, 8.09 Found: C, 36.37; H, 3.59; N, 7.07; S, 8.07.

The material is unstable upon recrystallization from chloroform-hexane and gives 8.14 g of recrystallized product, M.P. 87.5°-92° C. The mother liquor is concentrated and the residue is chromatographed on silica gel to give 7.9 g of the compound of Example 2. $n_D^{25}$ 1.4382.

Anal. Calc'd for $C_{12}H_{11}F_6NO_4$: C, 38.00; H, 2.92; N, 3.69. Found: C, 37.97; H, 2.92; N, 3.71.

Although the invention is described with respect to specific modifications, the details thereof are not to be construed as limitations except to the extent indicated in the following claims.

We claim:

1. A compound represented by the formula

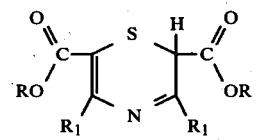

wherein R is selected from the group consisting of H and lower alkyl radicals and $R_1$ represents a perfluoroalkyl radical having from 1 to 3 carbon atoms.

2. A compound of claim 1 wherein R is ethyl and $R_1$ is perfluoroethyl.

3. A compound of claim 1 wherein R is ethyl and $R_1$ is trifluoromethyl.

4. A compound of claim 1 wherein R is hydrogen and $R_1$ is perfluoroethyl.

5. A compound of claim 1 wherein R is hydrogen.

6. A compound of claim 1 wherein R is lower alkyl.

7. A compound of claim 1 wherein R is ethyl and $R_1$ is perfluoropropyl.

8. A compound of claim 1 wherein R is butyl and $R_1$ is perfluoroethyl.

9. A compound of claim 1 wherein R is methyl and $R_1$ is perfluoroethyl.

10. Herbicidal compositions comprising an adjuvant and a herbicidally effective amount of a compound represented by the formula

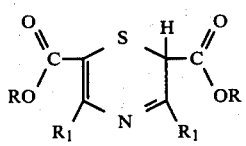

wherein R is selected from the group consisting of H and lower alkyl radicals and $R_1$ represents a perfluoroalkyl radical having from 1 to 3 carbon atoms.

11. A composition of claim 10 wherein R is ethyl and $R_1$ is perfluoroethyl.

12. A composition of claim 10 wherein R is ethyl and $R_1$ is trifluoromethyl.

13. A composition of claim 10 wherein R is hydrogen and $R_1$ is perfluoroethyl.

14. A composition of claim 10 wherein R is hydrogen.

15. A composition of claim 10 wherein R is lower alkyl.

16. A composition of claim 10 wherein R is ethyl and $R_1$ is perfluorpropyl.

17. A composition of claim 10 wherein R is butyl and $R_1$ is perfluoroethyl.

18. A composition of claim 10 wherein R is methyl and $R_1$ is perfluoroethyl.

19. A method for controlling the growth of undesirable plants which comprises applying to the locus of the seed a herbicidal amount of a compound represented by the formula

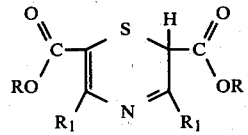

wherein R is selected from the group consisting of H and lower alkyl radicals and $R_1$ represents a perfluoroalkyl radical having from 1 to 3 carbon atoms.

20. A method of claim 19 wherein R is ethyl and $R_1$ is perfluoroethyl.

21. A method of claim 19 wherein R is ethyl and $R_1$ is trifluoromethyl.

22. A method of claim 19 wherein R is hydrogen or lower alkyl.

23. A method of claim 19 wherein R is ethyl and $R_1$ is perfluoropropyl.

24. A method of claim 19 wherein R is methyl and $R_1$ is perfluoroethyl.

25. A method for controlling the growth of undesirable plants which comprises applying to the plant a herbicidally effective amount of a compound represented by the formula

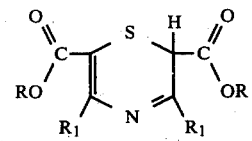

wherein R is selected from the group consisting of H and lower alkyl radicals and $R_1$ represents a perfluoroalkyl radical having from 1 to 3 carbon atoms.

26. A method of claim 25 wherein R is ethyl and $R_1$ is perfluoroethyl.

27. A method of claim 25 wherein R is ethyl and $R_1$ is trifluoromethyl.

28. A method of claim 25 wherein R is hydrogen.

29. A method of claim 25 wherein R is lower alkyl.

30. A method of claim 25 wherein R is ethyl and $R_1$ is perfluoropropyl.

31. A method of claim 25 wherein R is methyl and $R_1$ is perfluroroethyl.

32. A method of claim 25 wherein R is butyl and $R_1$ is perfluoroethyl.

33. A process for the preparation of a compound of claim 1 which comprises reacting a sulfur chloride selected from the group consisting of sulfur monochloride and sulfur dichloride with a 3-perfluoroalkyl-3-amino acrylate represented by the structural formula

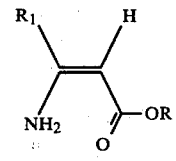

wherein R is selected from the group consisting of H and lower alkyl radicals and $R_1$ represents a perfluoroalkyl radical having from 1 to 3 carbon atoms.

34. The process of claim 33 wherein the 3-perfluoroalkyl-3-aminoacrylate is added to a reaction vessel containing said sulfur chloride.

35. The process of claim 33 wherein the sulfur monochloride is added to a reaction vessel containing said aminoacrylate.

36. A process of claim 33 wherein R is ethyl and $R_1$ is perfluoroethyl.

37. A process of claim 33 wherein R is ethyl and $R_1$ is trifluoromethyl.

38. A process of claim 33 wherein R is methyl and $R_1$ is perfluoroethyl.

39. A process of claim 33 where R is ethyl and $R_1$ is perfluoropropyl.

40. A process of claim 33 wherein R is hydrogen.

41. A process of claim 33 wherein R is lower alkyl.

42. A compound represented by the formula

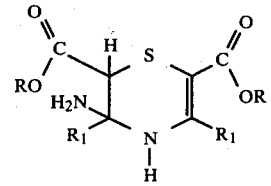

wherein R is selected from the group consisting of H and lower alkyl radicals and $R_1$ represents a perfluoroalkyl radical.

43. Diethyl 3-amino-3,5-bis(trifluoromethyl)-3,4-dihydro-2H-1,4-thiazine-2,6-dicarboxylate.

44. A method for controlling the growth of undesirable plants which comprises applying to the locus of the seed a herbicidal amount of a compound of claim 42.

45. A method of claim 44 wherein the compound is diethyl 3-amino-3,5-bis(trifluoromethyl)-3,4-dihydro-2H-1,4-thiazine-2,6-dicarboxylate.

46. A method for controlling the growth of undesirable plants which comprises applying to the plant a herbicidal amount of a compound of claim 42.

47. A method of claim 46 wherein the compound is diethyl 3-amino-3,5-bis(trifluoromethyl)3,4-dihydro-2H-1,4-thiazine-2,6-dicarboxylate.

48. A herbicidal composition comprising an adjuvant and a herbicidally effective amount of a compound represented by the formula

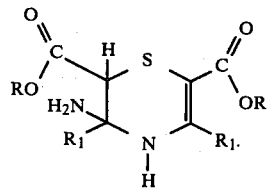

49. A composition of claim 48 wherein said compound is diethyl 3-amino-3,5-bis(trifluoromethyl)-3,4-dihydro-2H-1,4-thiazine-2,6-dicarboxylate.

* * * * *